United States Patent
Robertson (10) Patent No.: US 10,967,018 B2
(45) Date of Patent: *Apr. 6, 2021

(54) METHODS FOR EXTRACTION AND ISOLATION OF ISOPRENOID AND TERPENE COMPOUNDS FROM BIOLOGICAL EXTRACTS

(71) Applicant: Bradley Lee Robertson, Sausalito, CA (US)

(72) Inventor: Bradley Lee Robertson, Sausalito, CA (US)

(73) Assignee: Concentrated Consulting Group, LLC, Sausalito, CA (US)

( * ) Notice: Subject to any disclaimer, the term of this patent is extended or adjusted under 35 U.S.C. 154(b) by 281 days.

This patent is subject to a terminal disclaimer.

(21) Appl. No.: 15/095,174

(22) Filed: Apr. 11, 2016

(65) Prior Publication Data

US 2018/0344785 A1    Dec. 6, 2018

(51) Int. Cl.
  *A61K 36/18*   (2006.01)
  *A61K 31/352*  (2006.01)
  *A61K 36/185*  (2006.01)

(52) U.S. Cl.
  CPC ............ *A61K 36/18* (2013.01); *A61K 31/352* (2013.01); *A61K 36/185* (2013.01); *A61K 2236/15* (2013.01); *A61K 2236/33* (2013.01); *A61K 2236/35* (2013.01); *A61K 2236/37* (2013.01); *A61K 2236/39* (2013.01); *A61K 2236/53* (2013.01)

(58) Field of Classification Search
  None
  See application file for complete search history.

(56) References Cited

U.S. PATENT DOCUMENTS 10,323,014 B2 * 6/2019 Robertson ............ C07D 311/16
2017/0008870 A1 * 1/2017 Dibble ................. C07D 311/80

OTHER PUBLICATIONS

U.S. Appl. No. 15/095,176, filed Apr. 2016, Robertson; Bradley Lee.*

* cited by examiner

*Primary Examiner* — Michael Barker
(74) *Attorney, Agent, or Firm* — KSIP; Kelsey Stout (57) ABSTRACT

A method for the extraction and isolation of the terpene and isoprenoid compounds from plant material, followed by a centrifugal force induced selective crystallization of isoprenoids resulting in a separation of terpene and isoprenoid fractions. This this method is suitable for the extraction of cannabinoids from *Cannabis* and the enrichment tetrahydrocannabinolic acid and reduction of tetrahydrocannabinol in an extract.

24 Claims, 8 Drawing Sheets

| Documented Effect | Study | Literature Reference |
|---|---|---|
| Anti-inflammatory | Evaluation of the cyclooxygenase inhibiting effects of six major cannabinoids isolated from Cannabis sativa | Ruhaak LR, Felth J, Karlsson PC, Rafter JJ, Verpoorte R, Bohlin L. (2011), Biological and Pharmaceutical Bulletin 34 (5): 774–8, doi:10.1248/bpb.34.774, PMID 21532172 |
| Neuroprotective to Oxidative Stress | Effects of cannabinoids Δ(9)-tetrahydrocannabinol, Δ(9)-tetrahydrocannabinolic acid and cannabidiol in MPP(+) affected murine mesencephalic cultures | Moldzio R, Pacher T, Krewenka C, Kranner B, Novak J, Duvigneau JC, Rausch WD. (2012), Phytomedicine 19 (8-9): 819–24, doi:10.1016/j.phymed.2012.04.002, PMID 22571976 |
| Antiemetic (Anti-Vomitting) | The tetrahydrocannabinol and tetrahydrocannabinolic acid content of cannabis products | Baker PB, Taylor BJ, Gough TA. (1981), Journal of Pharmacy and Pharmacology 33 (6): 369–72, doi:10.1111/j.2042-7158.1981.tb13806.x, PMID 6115009 |
| Anti-Prostate Cancer | Non-THC cannabinoids inhibit prostate carcinoma growth in vitro and in vivo: pro-apoptotic effects and underlying mechanisms | De Petrocellis L, Ligresti A., Moriello A.S., Iappelli M., Verde R., Stott C.G., Cristino L., Orlando P., and Di Marzo V. (2013), British Journal of Pharmacology 168 (1): 79–102, doi:10.1111/j.1476-5381.2012.02027.x, PMC 3570006 |
| THCA stability in vivo | Studies on the metabolism of the Delta-9-tetrahydrocannabinol precursor delta-9-tetrahydrocannabinolic acid A (Delta9-THCA-A) in rat using LC-MS/MS, LC-QTOF MS and GC-MS techniques | Jung J, Meyer MR, Maurer HH, Neusüss C, Weinmann W, Auwärter V. (2009), Journal of Mass Spectrometry 44 (10): 1423–33, doi:10.1002/jms.1624, PMID 19728318 |

Fig. 3

THCA ($C_{22}H_{30}O_4$) →[heat >105°C] THC ($C_{21}H_{30}O_2$) + $CO_2$

| sample | Plant material | | Initial extract | | | centrifugally separated crystals | | | |
|---|---|---|---|---|---|---|---|---|---|
| | weight | % THCA by weight | weight | % THCA by weight | % yield (extraction) | weight | % THCA by weight | % yeild (crystallization) | % yield (overall process) |
| Plant Material #1 | 100 g | 17.8% | 12.2 g | 49.9% | 34.2% | 5.9g | 94.5% | 91.6% | 31.3% |

Fig. 6

METHODS FOR EXTRACTION AND ISOLATION OF ISOPRENOID AND TERPENE COMPOUNDS FROM BIOLOGICAL EXTRACTS

CROSS-REFERENCE TO RELATED APPLICATIONS

This application claims the benefit of U.S. Provisional Application Ser. No. 62/146,198 entitled "A Method for Extracting Cannabinoids and Terpenes through Centrifugation", filed Apr. 10, 2015.

FIELD OF THE INVENTION

The present invention relates to a method for the extraction and isolation of natural compounds. More particularly, the present invention relates to a method suitable for the extraction of terpene, isoprenoid, and prenylated chalconoid compounds from the flowers and leaves of plants, followed by a fractionation in which terpene and isoprenoid compounds are selectively separated from each other, with the separated compounds being suitable for use in scenting, flavoring, antimicrobial, medicinal, or nutritional supplement applications.

BACKGROUND OF THE INVENTION

Terpenes and isoprenoids are the major constituents of the essential oils of plants and flowers. Plant essential oils are used in fragrances as additives to food products and perfumery. These essential oils are also used in medicine and alternative medicines.

Figure 1:
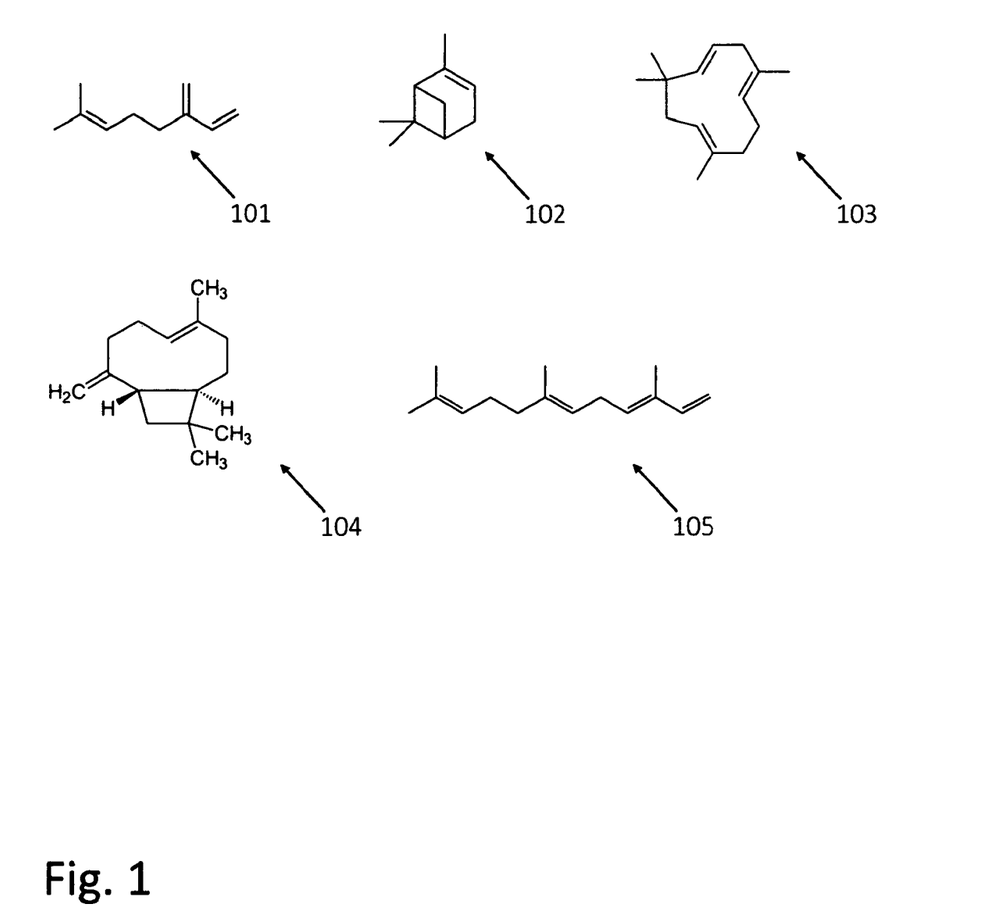
FIG. 1 shows the chemical structure of the terpene compounds myrcene, pinene, humulene, caryophyllene, and farnesene.

Terpenes are hydrocarbon compounds that account for many of the aromas in evergreen trees or citrus, as well as other aromatic plants such as lemongrass or hops used in beer brewing. Major terpenes include myrcene (herbaceous, citrus-like aroma), β-pinene (piney aroma), β-caryophyllene (peppery or clove-like aroma), farnesene (green apple aroma), and α-humulene (hoppy aroma). The structures of these terpenes are shown in FIG. 1. In addition to aroma, some of these terpenes have been found to have medicinal effects. Myrcene has an analgesic effect (Lorenzetti et al 1991). Humulene has been shown to have anti-inflammatory and anti-allergic effects (Passosa et al, 2007). Caryophyllene has been shown to have an anti-inflammatory effect in mice (Gertsch et al, 2008).

Isoprenoid compounds are chemically similar to terpenes, though isoprenoid compounds contain additional (non-hydrocarbon) functional groups such as carbonyl, carboxylic acid, or phosphate moieties. Plant isoprenoid compounds have been used extensively for their aromatic qualities in cooking, contributing to the flavors and scents such as cinnamon, cloves, ginger, eucalyptus, and mustard seed, as well as to the colors of plants such orange turmeric or red tomatoes. Medicinal isoprenoids including cannabinoids found in *Cannabis*, ginkgolide and bilobalide found in *Ginkgo biloba*, and the curcuminoids found in turmeric.

In recent years, the use of *Cannabis* and *Cannabis* extracts for medicinal purposes has increased. However, the complex chemical composition of *Cannabis* and *Cannabis* extracts presents several complications for medicinal use. First, while some components of *Cannabis* have medically useful characteristics, other compounds result in the undesirable psychoactive and narcotic effects that limit the medical usefulness of *Cannabis* in many applications and patients. Further, the mixed composition of plant-based materials (which varies due to strain, cultivation method, preparation, or age) makes safety and efficacy testing difficult, as various compounds may have synergistic or interfering effects. In addition, while numerous compounds in *Cannabis* have been shown to have medicinal use, a small number of psychoactive compounds from *Cannabis* are scheduled by the federal government as controlled substances. Without isolated and purified compounds of medicinal value from *Cannabis*, pharmaceutical usage of specific *Cannabis*-derived compounds is greatly limited.

Figure 2A:
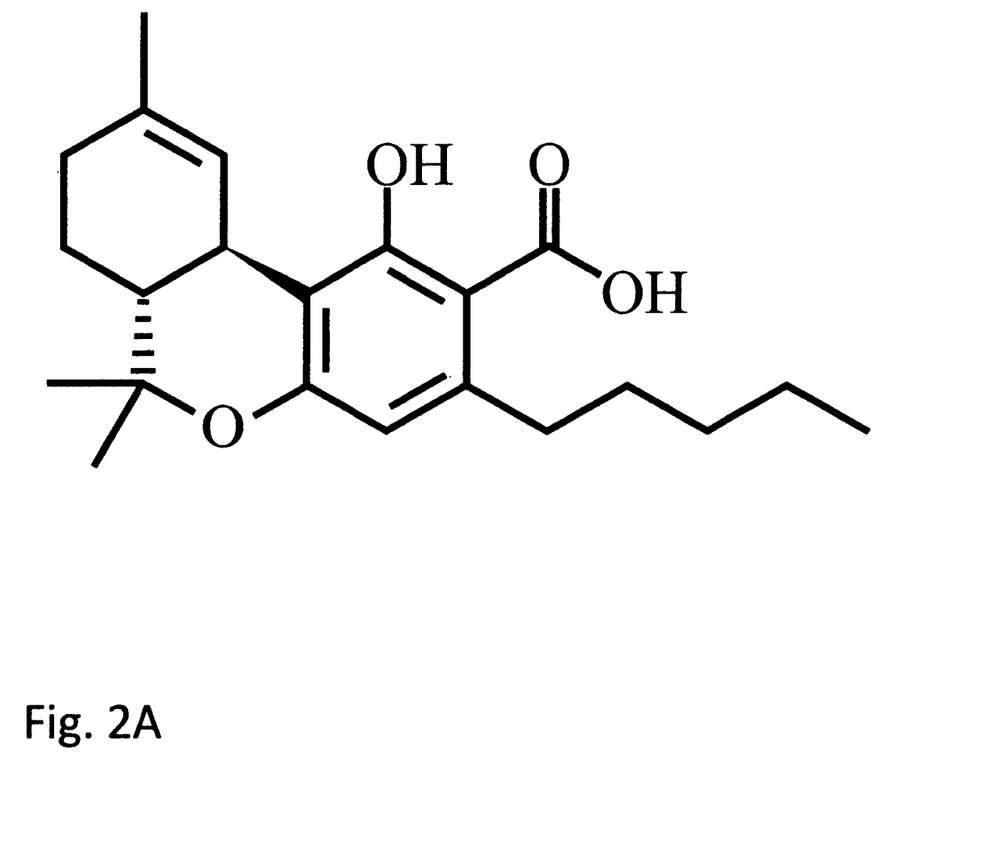
FIG. 2*a* shows the chemical structure of the non-psychoactive compound tetrahydrocannabinolic acid (THCA).
Figure 2B:
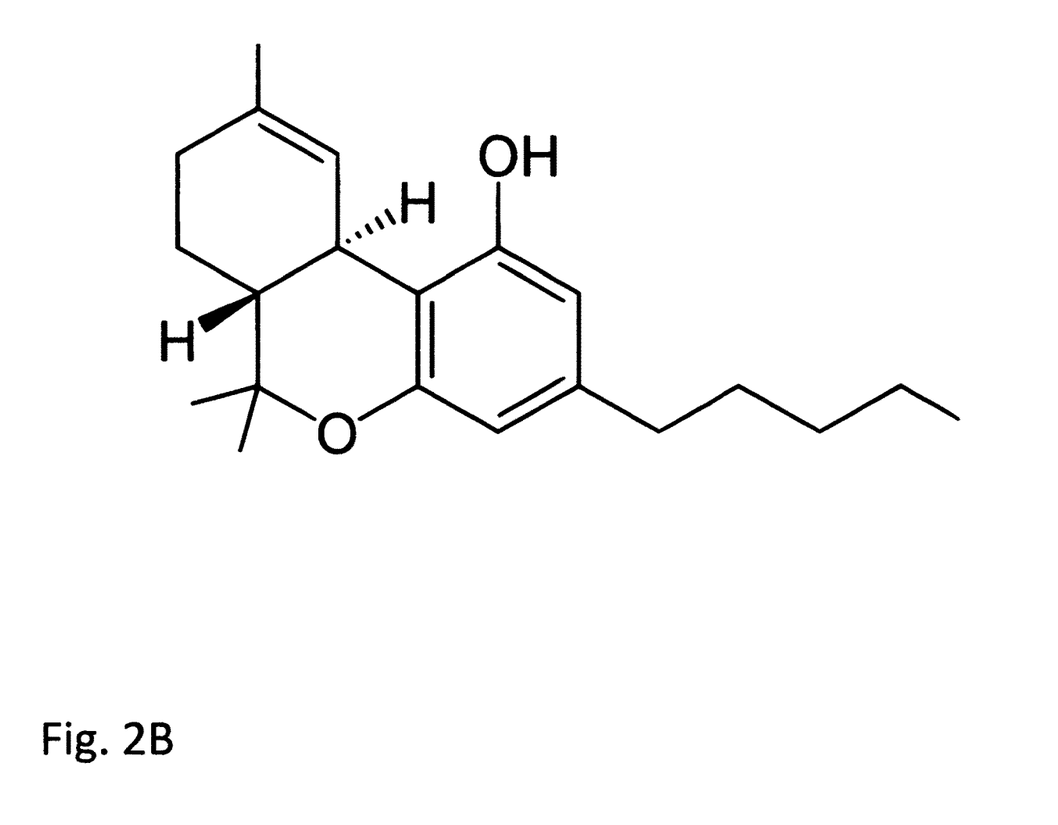
FIG. 2*b* shows the chemical structure of tetrahydrocannabinol (THC).

The structures of the isoprenoid compounds tetrahydrocannabinolic acid (THCA, also known as 2-COOH-THC) and tetrahydrocannabinol (THC, also known as Δ9-THCA) are shown in FIG. 2a and FIG. 2b, respectively. THC is the primary psychoactive compound in *Cannabis*, while THCA is neither psychoactive nor federally scheduled as a controlled substance (Stark, 1990, *Marijuana Chemistry: Genetics, Processing, Potency*). Academic studies have shown that isolated THCA has a number of medically useful characteristics, such as anti-inflammatory properties, anti-cancer effects, and antiemetic effects. A table of these studies is shown in FIG. 3.

Figure 4:
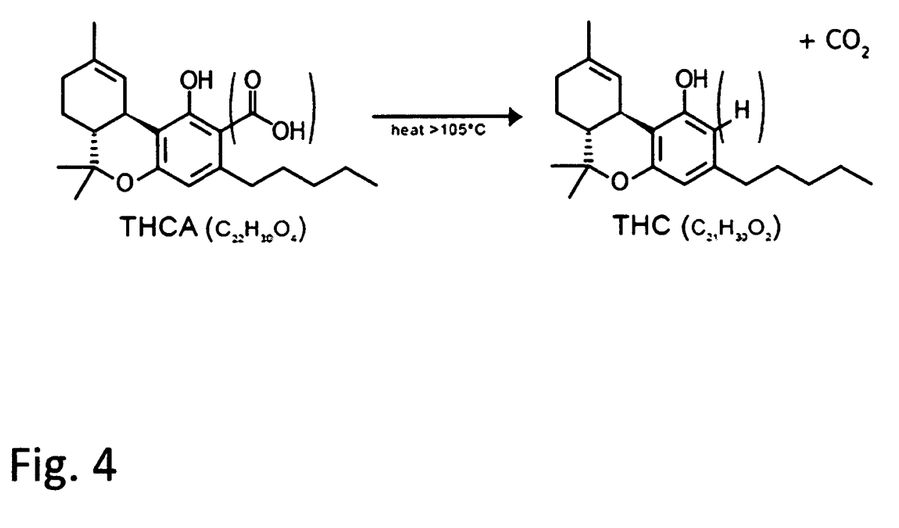
FIG. 4 shows the decarboxylation reaction by which TCHA is degraded into THC.

THC is a chemical degradation product of THCA. FIG. 4 shows the reaction by which THCA is decarboxylated and converted to THC (and carbon dioxide). The reaction shown in FIG. 2 is greatly accelerated by heat; while the THCA is the predominant compound in living and freshly harvested *Cannabis*, THC is formed rapidly as *Cannabis* is burned (e.g., by smoking). Small amounts of THC are formed slowly from THCA as *Cannabis* is dried or aged. In addition to heat instability, the degradation of purified THCA to THC is accelerated by ultraviolet light, oxygen, or acidic conditions (Zoller et al., 2000). Notably, THCA is stable in vivo, as shown by mass spectrometry in a study of THCA metabolism in rat by Jung et al., 2009.

Current methods for purification of THCA from THC involve expensive and time intensive methods that do not scale well, such a high-pressure liquid chromatography. While current THCA purification methods are suitable for the production of analytical or research quantities of THCA, medicinal or pharmaceutical production would require a less expensive and more robust process.

There is currently a lack of data available with respect to the effects of various plant-based medicines, remedies or health-promoting agents—even widely used remedies may not have undergone substantial clinical testing. The lack of data is particularly acute with respect to historically controlled substances, such as *Cannabis*. The effects of plant-based products may vary significantly between strains, between preparations, and between delivery routes. The lack of highly purified and stable plant based medicinal compounds is one of the primary impediments to meaningful testing of the medicinal properties of these compounds, or to any pharmaceutical use.

There exists an unmet need to develop a method for the rapid extraction of THCA from *Cannabis*, followed by purification of THCA from THC and other *Cannabis* compounds, psychoactive or otherwise. There further exists an unmet need that this purification method be inexpensive and robust, so as to be suitable to scaled production.

SUMMARY OF THE INVENTION

It is an object of the present invention to provide a method by which terpene and isoprenoid compounds can be rapidly and cost effectively extracted from plant material or other biomass.

It is an additional object of the present invention to provide a method by which the terpene and isoprenoid extract can be economically fractionated such that relatively pure terpene and isoprenoid fractions can be separated for use or further purification.

It is an object of the present invention to provide a method that allows for the extraction of terpene and isoprenoid compounds from the flowers of *Cannabis* species, with the resulting extract then being subject to a fractionation process by which the terpene compounds present in the extract are separated from the isoprenoid compounds, with this isolated isoprenoid fraction containing cannabinoids that are subject to a crystallization step resulting in the selective isolation of highly-purified tetrahydrocannabinolic acid.

Concepts were developed for the extraction of terpene and isoprenoid compounds from *Cannabis* plant material (or *Cannabis* cell culture), with the plant material first being subject to a maceration and then being chilled, with the chilled plant material then being introduced into a pre-chilled solvent extraction chamber, with the plant material and solvent extraction chamber then being degassed, with liquefied and chilled n-propane then being introduced into the degassed solvent extraction chamber containing plant material such that the liquid n-propane solubilizes the terpene and isoprenoid compounds from plant material, with the liquid n-propane containing dissolved plant compounds then being separated from the residual plant material by filtration, with the filtered liquid n-propane containing dissolved plant compounds then being treated such that the n-propane is recovered leaving behind an extract comprised of the compounds solubilized from the plant material, including terpene and isoprenoid compounds. This extract, containing compounds solubilized from the plant material, including terpene and isoprenoid compounds, is then placed on a surface, with this surface then being placed into a temperature controlled chamber, with this temperature controlled chamber then being subject to vacuum, with the temperature and vacuum being such that after a certain period of time polymorphic crystals begin to form, at which point the extract containing the polymorphic crystals is removed from the extraction chamber and placed into a centrifuge, with the extract and polymorphic crystals then being subject to centrifugal separation, with the pelleted polymorphic crystals containing primarily isoprenoid compounds being separated from the terpene compound-rich supernatant, and with the terpene compound-rich supernatant then being filtered to remove residual small isoprenoid crystals.

The primary embodiment of this invention is a method in which terpene compounds and isoprenoid compounds, including cannabinoid compounds, are extracted from *Cannabis* plant material through use of a solvent, with the terpene and cannabinoid containing extract then being subject to increased gravitational force through centrifugation, with this centrifugation affecting the separation of isolated cannabinoids from terpenes.

Additional object features and advantages of the invention will become more readily apparent from the following detailed description of various preferred embodiments.

BRIEF DESCRIPTION OF THE FIGURES

FIG. 3 is a table showing academic studies that have shown medicinal effects of THCA, and the stability of THCA in vivo.

DETAILED DESCRIPTION OF THE INVENTION

With reference to FIG. 1, the structures of some of the most abundant terpene compounds found in the female flower of *Cannabis* are shown; 101 is myrcene, 102 is pinene, 103 is humulene, 104 is caryophyllene, and 105 is farnesene.

Figure 5A:
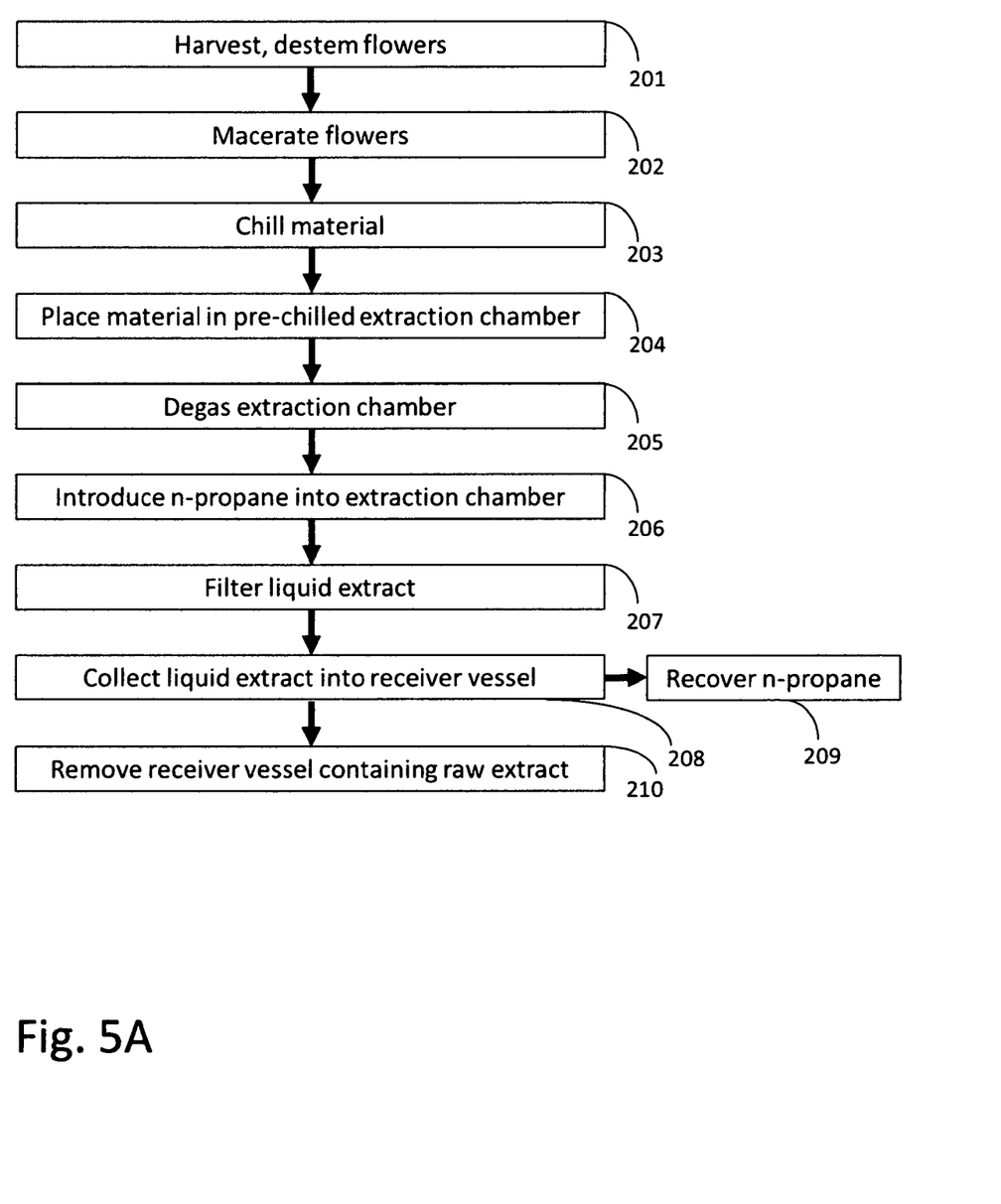
FIG. 5*a* is a box diagram showing the extraction process by which terpene and isoprenoid compounds are extracted from *Cannabis*, representing one element of the primary embodiment of this invention.
Figure 5B:
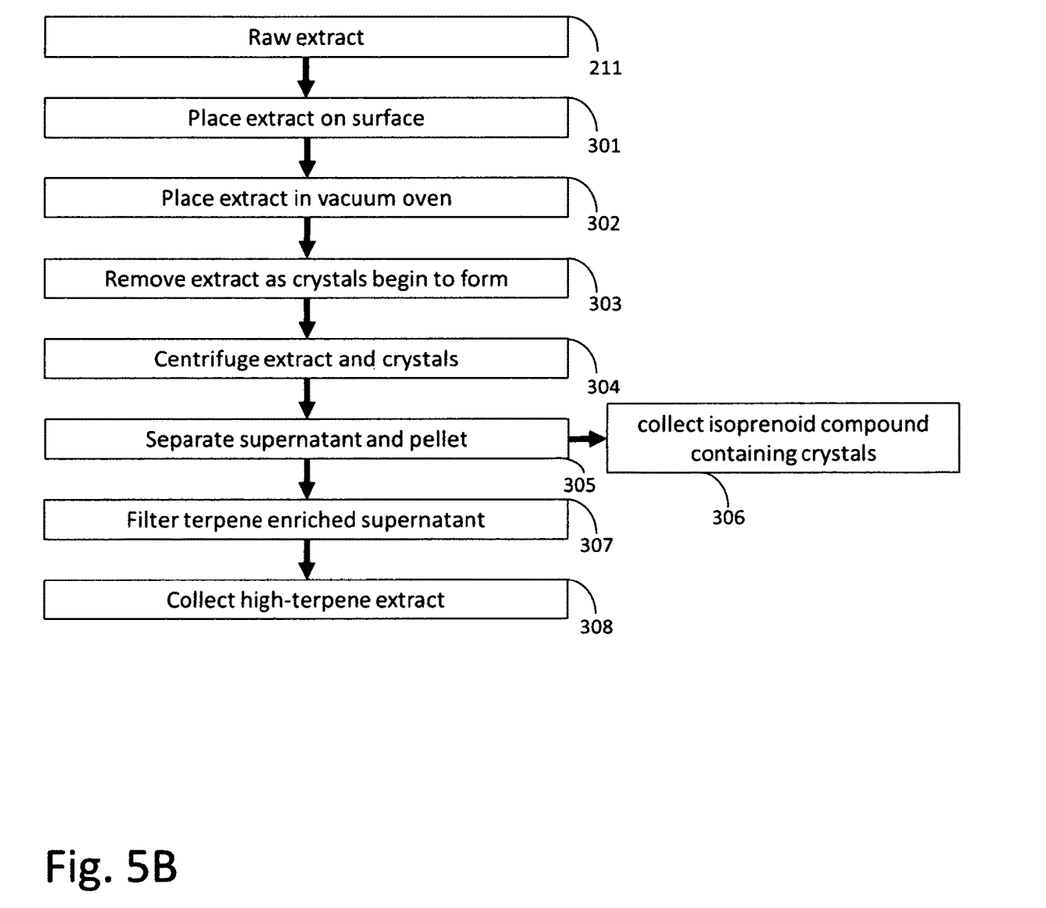
FIG. 5*b* is a box diagram showing the post-extraction fractionation process by which isoprenoid and terpene compounds are separated from *Cannabis* extracts, representing a second element of the primary embodiment of this invention.

With reference to FIG. 5*a* and FIG. 5*b*, the primary embodiment of this invention is shown. FIG. 5*a* shows a flow chart representing the initial extraction process by which terpene compounds and isoprenoid compounds, including cannabinoid compounds, are extracted from *Cannabis* plant material. In 201, the female flowers of *Cannabis* are harvested and destemmed. In 202 the destemmed flowers from 201 are shredded, macerated, ground, milled, or otherwise reduced in size. In 203, the macerated flower material from 202 is chilled. In 204, the chilled flower material from 203 is placed into a pre-chilled extraction chamber. In 205, the extraction chamber is sealed and degassed. In 206, subcritical (liquid) n-propane is introduced into the degassed extraction chamber from 205, with this n-propane dissolving and extracting chemical compounds from the flower material. In 207, the liquid n-propane containing dissolved compounds extracted from the flower material from 206 is separated from the flower material solids by filtration. In 208, the filtered liquid n-propane containing dissolved compounds extracted from the flower material from 207 is collected into a receiver vessel. In 209, the n-propane is removed from the extract contained in the receiver vessel in 208. In 210, the extract-containing receiver vessel, from which n-propane had been recovered in 209, is removed from the extraction chamber apparatus, and this raw extract is ready for further fractionation.

In some embodiments, the flowers are not dried. In one preferred embodiment, the flowers are reduced in size to 1-3 mm. In some embodiments, the flowers are not reduced in size. In one preferred embodiment, the flowers are chilled to between 0° C. and −100° C. prior to extraction. In one preferred embodiments the extraction chamber is pre-chilled to between 0° C. and −100° C. In one preferred embodiment, the n-propane is pre-chilled to between 0° C. and −100° C. before introduction into the extraction chamber. In some embodiments, there is a soak time upon introduction of the n-propane into the extraction chamber prior to separating the n-propane containing dissolved compounds from the plant material. In other embodiments there is no soak time, and separation of the n-propane containing dissolved compounds from the plant material is immediate. In some embodiments, the n-propane is recovered from the receiver vessel by use of differential pressure or temperature such that the n-propane becomes a gas and is readily removable, as is known in the art.

FIG. 5b shows a flow chart representing an initial purification step following the extraction process from FIG. 5a. In 211, the raw extract removed from the receiver vessel 210 (from FIG. 5a) it taken for fractionation. In 301, the raw extract from 211 is placed on a surface. In 302, the raw extract on a surface from 301 is placed in a vacuum oven, with this oven then being closed and purged of air. The extract is incubated in the vacuum oven until polymorphic crystals begin to form, at which point it is removed, 303. In 304, the extract removed from the vacuum oven containing polymorphic crystals from 303 is placed into a temperature controlled centrifuge, with the centrifuge then being activated so as to separate the solid crystals from the liquid phase of the extract. In 305, the centrifugally pelleted crystal fraction and liquid supernatant fraction from 304 are separated. In 306, the crystals from 305, which contain isoprenoid compounds and cannabinoid compounds, are collected. In 307, the liquid supernatant fraction from 305, which is rich in terpenes, is filtered to remove any residual crystals. In 308, the filtered terpene-rich extract from 307 is recovered.

In some embodiments the surface is a stainless steel sheet. In other embodiments, the surface is wax paper, a glass crystallization dish, foil sheeting, or other materials known in the art. In one preferred embodiment, the vacuum oven is at a temperature between 21° C. and 60° C., and at a pressure of less than one atmosphere. In some embodiments, the centrifuge (including but not limited to a continuous tubular centrifuge, scroll centrifuge or swing bucket centrifuge) is spun at a rate between 10 rpms to 50,000 rpms at a temperature range between −60° C. to 200° C. for a time which is sufficient to separate terpenes and isoprenoid compounds. In one preferred embodiment, the centrifuge is held at a temperature between 21° C. and 60° C., and activated so as to exert 500-2000× gravity upon the extract containing terpenes and isoprenoid compounds. In some embodiments, the centrifugally pelleted crystal fraction and liquid supernatant fraction are separated by filtration. In other embodiments the centrifugally pelleted crystal fraction and liquid supernatant fraction are separated by decanting.

In some embodiments, the process may further comprise steps of filtering the condensate during centrifugation to collect water insoluble material and extracting the insoluble material. In some embodiments precipitants are added to the extract, in order to affect the precipitation of impurities, which will then be subsequently filtered out. In some embodiments precipitants are added to the extract in order to affect the selective precipitation of target isoprenoid compounds, with subsequent centrifugation or filtration being used to harvest these target compounds. In one preferred embodiment, sucrose crystals (sugar) can be used as a selective precipitant for THCA relative to other cannabinoids found in a non-polar solvent extract of cannabinoids—with this selectivity owing to the hydrophilic nature of sucrose and the relatively greater hydrophilic nature of THCA to other cannabinoids (resulting from the carboxylic acid moiety on THCA).

Figure 6:
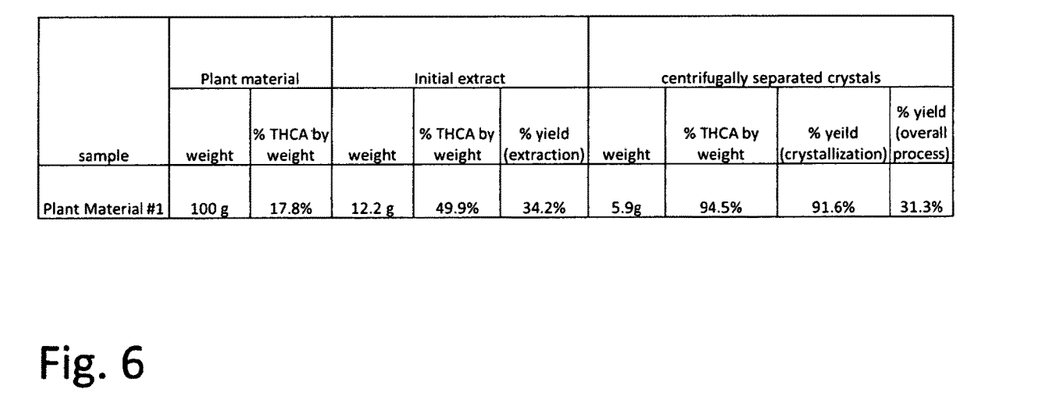
FIG. 6 is a table showing the enrichment of THCA from plant biomass to enriched extract through use of the primary embodiment of this invention, with THCA values shown having been measured by mass spectrometry (MS) following separation by high pressure liquid chromatography.

As an example of the primary embodiment, consider the preparation of a highly pure THCA *Cannabis* extract meant for use in research into the potential treatment of a human disease state, such as prostate cancer or various inflammatory diseases (THCA has been indicated as potentially useful in treating these disease states, as in known in the art, with some examples being shown in FIG. 3). While medicinal benefits have been shown for THCA, the narcotic effects of delta-9 THC and sedative effects of cannabidiol (CBD) are undesirable in medicinal applications. Through use of the method of the primary embodiment, the purity of THCA from a sample of *Cannabis* can be greatly increased, with a subsequent reduction in the concentration of delta-9 THC and CBD compounds, with this material having little or no intoxicating effect on the patient being treated. An example of the enrichment of THCA through use of the method of the primary embodiment is shown as a table in FIG. 6. Briefly, 100 g of dried, mature *Cannabis* flower, with an initial THCA content of 17.8% w/w, is subject to extraction by the method of the primary embodiment using subcritical n-propane as a solvent, with the initial extract having 49.5% THCA w/w, and the centrifugally separated crystals being 94.5% THCA w/w. THCA analysis was done using an AGILENT 1100 (Agilent, Santa Clara, Calif.) HPLC with G1946D mass spectrometry detector using methods known in the art of liquid chromatography coupled mass spectrometry.

In some embodiments, the starting material in the process, or condensates, may be derived from any *Cannabis* product containing the target compound(s), and most preferably from a stage in the processing in which higher molecular weight cannabinoids and/or terpenes are still intact.

In some embodiments, the extract can also be provided in a variety of forms, including but not limited to oils and other concentrated liquid forms, or in dried forms such as but not limited to crystals, powders and the like.

In some embodiments, the process may be operated continuously including but not limited to use of screen centrifuges or scroll centrifuges and as such is particularly suitable for use in large scale commercial production of extracts from crude *Cannabis* extracts or plant material.

In some embodiments, Büchner filtration, or other types of differential pressure filtration, is used in order to speed the separation of liquids and solids contained in solvent extracts.

In some embodiments other solvents are used for the initial extraction, including but not limited to supercritical carbon dioxide, hexane, or ether.

In some embodiments the terpene containing fraction is used directly as a side-product.

In some embodiments, the terpene or cannabanoid isolate is subject to further purification for purposes of isolating at least one target compound(s) from the extract by thermal fractionation (such as distillation, e.g. vacuum distillation, and related processes), chromatographic separation (such as normal and reverse phase or affinity purification), recrystallization or combinations thereof. In these and other embodiments it may also be preferable to adjust pH of the condensate to enhance precipitation of the at least one target compound(s).

Although described with reference to preferred embodiments of the invention, it should be recognized that various changes and/or modifications of the invention can be made without departing from the spirit and scope of the invention. In any case, the invention is only intended to be limited by the scope of the following claims.

What is claimed is:

1. A method of extracting terpene and isoprenoid compounds from plant material and for selectively enriching the concentration of isoprenoid compounds in a fraction of this extract comprising the steps of:
  a. placing plant material into an extraction chamber, wherein the plant material comprises female flowers of *Cannabis*;
  b. degassing the extraction chamber;
  c. introducing chilled solvent into the extraction chamber such that extract-containing solvent forms;
  d. filtration of the extract-containing solvent;
  e. removal of the extract-containing solvent from the extraction chamber;
  f. placing extract-containing solvent on a surface prior to placing the extract-containing solvent into a centrifuge vessel, the surface being capable of being placed into a vacuum oven;
  g. placing the extract-containing solvent into a centrifuge vessel;
  h. centrifuging the centrifuge vessel to promote formation of crystals and to separate said crystals from supernatant solvent; and
  i. collecting the crystals.

2. The method of claim 1 wherein the crystals are over 90% pure THCA.

3. The method of claim 1 further comprising the step of: sorting and reducing the size of the plant material by destemming and grinding the plant material prior to placing the plant material in the extraction chamber.

4. The method of claim 1 further comprising the step of: chilling the plant material prior to placing plant material into the extraction chamber.

5. The method of claim 1 further comprising the step of: pre-chilling the extraction chamber prior to placing plant material into the extraction chamber.

6. The method of claim 1 further comprising the step of: placing said extract-containing solvent on a surface into a vacuum oven in order to accelerate crystal formation prior to placing the extract-containing solvent into a centrifuge vessel.

7. The method of claim 1 further comprising the step of: waiting for crystals to begin to form on the surface prior to placing the extract-containing solvent into a centrifuge vessel.

8. The method of claim 1 further comprising the steps of:
  waiting for crystals to begin to form on the surface;
  placing the surface and extract-containing solvent into a vacuum oven;
  closing the vacuum oven;
  purging the vacuum oven of air;
  incubating the extract in the vacuum oven until polymorphic crystals begin to form; and,
  removing the surface and extract-containing solvent from the vacuum oven.

9. The method of claim 1 further comprising the step of: placing the surface and the extract-containing solvent into a vacuum oven in order to accelerate crystal formation.

10. The method of claim 1 wherein the solvent is subcritical n-propane, butane, hexane, pentane, ether, ethyl acetate, heptane, toluene, naphtha, methanol, isopropanol, butanol, or combinations thereof.

11. The method of claim 1 wherein the solvent is supercritical carbon dioxide.

12. The method of claim 1 wherein various extracts of *Cannabis* are substituted for the plant material.

13. A method of extracting terpene and isoprenoid compounds from plant material and for selectively enriching the concentration of isoprenoid compounds in a fraction of this extract comprising the steps of:
  a. placing plant material into an extraction chamber, wherein the plant material comprises female flowers of *Cannabis*;
  b. degassing the extraction chamber;
  c. introducing chilled solvent into the extraction chamber such that extract-containing solvent forms;
  d. filtration of the extract-containing solvent;
  e. removal of the extract-containing solvent from the extraction chamber;
  f. addition of sugar, salt, or other precipitant to the extract-containing solvent, wherein the precipitant is chosen for selectively precipitating THCA;
  g. placing the extract-containing solvent into a centrifuge vessel;
  h. centrifuging the centrifuge vessel to promote formation of crystals and to separate said crystals from supernatant solvent; and
  i. collecting the crystals.

14. The method of claim 13 wherein the precipitant is chosen for selectively precipitating delta-9 THC.

15. The method of claim 13 wherein the precipitant is chosen for selectively precipitating CBD.

16. The method of claim 1 further comprising the step of:
  addition of acid, base, or buffering compounds to the solvent or solvent-containing extract so as to regulate the pH of the system and to promote differential crystallization.

17. A method of extracting terpene and isoprenoid compounds from plant material and for selectively enriching the concentration of isoprenoid compounds in a fraction of this extract comprising the steps of:
  a. placing plant material into an extraction chamber, wherein the plant material comprises female flowers of *Cannabis*;
  b. degassing the extraction chamber;
  c. introducing chilled solvent into the extraction chamber such that extract-containing solvent forms;
  e. removal of the extract-containing solvent from the extraction chamber;
  f. addition of precipitant, wherein the precipitant is chosen for selectively promoting the precipitation of delta-9 THC
  g. Buchner filtration of the solvent containing extract prior to centrifugation
  h. placing the extract-containing solvent into a centrifuge vessel;
  i. centrifuging the centrifuge vessel to promote formation of crystals and to separate said crystals from supernatant solvent; and
  j. collecting the crystals.

18. The method of claim 17
  wherein the precipitant is chosen for selectively promoting the precipitation of CBD.

19. The method of claim 17
  wherein the precipitant is chosen for selectively promoting the precipitation of gums, waxes, phospholipids, protein, lipoprotein, carbohydrates, sugars, nucleic acids, coenzymes, or metal ions.

20. The method of claim 1 further comprising the step of: collection of a terpene-rich fraction.

21. The method of claim 1 wherein the solvent is a non-polar liquid organic solvent chilled to between 0° C. and −100° C.

22. The method of claim 13 wherein the solvent is subcritical n-propane, butane, hexane, pentane, ether, ethyl acetate, heptane, toluene, naphtha, methanol, isopropanol, butanol, or combinations thereof.

23. The method of claim 17 wherein the solvent is subcritical n-propane, butane, hexane, pentane, ether, ethyl acetate, heptane, toluene, naphtha, methanol, isopropanol, butanol, or combinations thereof.

24. The method of claim 1, further comprising the steps of:
- sorting and reducing the size of the plant material by destemming and grinding the plant material prior to placing the plant material in the extraction chamber;
- chilling the plant material prior to placing plant material into the extraction chamber;
- pre-chilling the extraction chamber prior to placing plant material into the extraction chamber;
- placing the surface and extract-containing solvent into a vacuum oven;
- closing the vacuum oven;
- purging the vacuum oven of air;
- incubating the extract in the vacuum oven until polymorphic crystals begin to form; and,
- removing the surface and extract-containing solvent from the vacuum oven;
- wherein the solvent is subcritical n-propane, butane, hexane, pentane, ether, ethyl acetate, heptane, toluene, naphtha, methanol, isopropanol, butanol, or combinations thereof; and,
- wherein the crystals are over 90% pure THCA.

\* \* \* \* \*

UNITED STATES PATENT AND TRADEMARK OFFICE
CERTIFICATE OF CORRECTION

| | |
|---|---|
| PATENT NO. | : 10,967,018 B2 |
| APPLICATION NO. | : 15/095174 |
| DATED | : April 6, 2021 |
| INVENTOR(S) | : Bradley Lee Robertson |

It is certified that error appears in the above-identified patent and that said Letters Patent is hereby corrected as shown below:

In the Specification

Column 1, Lines 9-12, Should read:
This application claims the benefit of U.S. Provisional Application Ser. No. 62/146,198 entitled "A Method for Extracting and Purifying Cannabinoids and Terpenes through Centrifugation", filed Apr. 10, 2015.

Signed and Sealed this
Twentieth Day of June, 2023

Katherine Kelly Vidal
*Director of the United States Patent and Trademark Office*